United States Patent
Burbank et al.

(10) Patent No.: US 7,207,996 B2
(45) Date of Patent: Apr. 24, 2007

(54) DOPPLER DIRECTED SUTURING AND COMPRESSION DEVICE AND METHOD

(75) Inventors: Fred H. Burbank, San Juan Capistrano, CA (US); Michael L. Jones, Capistrano Beach, CA (US); Greig E. Altieri, Laguna Beach, CA (US); R. J. Serra, Irvine, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 787 days.

(21) Appl. No.: 10/115,422

(22) Filed: Apr. 4, 2002

(65) Prior Publication Data
US 2003/0191391 A1 Oct. 9, 2003

(51) Int. Cl.
*A61B 17/04* (2006.01)
*A61F 6/06* (2006.01)

(52) U.S. Cl. .............. 606/151; 600/446; 600/453; 128/831; 128/887

(58) Field of Classification Search .......... 606/151, 606/207; 600/446, 453
See application file for complete search history.

(56) References Cited

U.S. PATENT DOCUMENTS

| | | |
|---|---|---|
| 3,411,505 A | 11/1968 | Nobis |
| 3,777,740 A | 12/1973 | Hokanson |
| 3,779,248 A | 12/1973 | Karman |
| 4,120,302 A | 10/1978 | Ziegler |
| 4,226,240 A | 10/1980 | Walker, Jr. |
| 4,292,960 A | 10/1981 | Paglione |
| 4,428,379 A | 1/1984 | Robbins et al. |
| 4,509,528 A | 4/1985 | Sahota |
| 4,650,466 A | 3/1987 | Luther |
| 4,757,823 A | 7/1988 | Hofmeister et al. |
| 4,994,069 A | 2/1991 | Ritchart et al. |
| 5,037,430 A | 8/1991 | Hasson |
| 5,081,997 A | 1/1992 | Bosley, Jr. et al. |
| 5,108,408 A | 4/1992 | Lally |
| 5,201,314 A | 4/1993 | Bosley et al. |
| 5,226,911 A | 7/1993 | Chee et al. |
| 5,275,166 A | 1/1994 | Vaitekunas et al. |
| 5,289,831 A | 3/1994 | Bosley |
| 5,336,231 A | 8/1994 | Adair |
| 5,383,922 A | 1/1995 | Zipes et al. |
| 5,427,108 A * | 6/1995 | Bollinger .............. 600/461 |

(Continued)

FOREIGN PATENT DOCUMENTS

| | | |
|---|---|---|
| DE | 195 28 440 A | 2/1997 |
| DE | 200 22 012 U1 | 5/2001 |
| EP | 0 472 368 | 2/1992 |

(Continued)

OTHER PUBLICATIONS

Barth, Klemens H. et al., "Long Term Follow–up of Transcatheter Embolization With Autologous Clot, Oxycel and Gelfoam in Domestic Swine", *Investigative Radiology*, May–Jun. 1977, vol. 12, pp. 273–290.

(Continued)

*Primary Examiner*—Gary Jackson
(74) *Attorney, Agent, or Firm*—Edward J. Lynch; Duane Morris LLP (57) ABSTRACT

A compression and ligation device includes a pair of jaws including one or more Doppler chips oriented to send and receive Doppler signals across the jaws, to assist a practitioner in determining whether or not a uterine artery is between the jaws. A suture leader with an attached suture can be pushed through a channel on one of the jaws, through tissue behind the uterine artery, into another channel on the other jaw, and proximally out the device so that the practitioner can ligate the artery and effect hemostasis.

17 Claims, 3 Drawing Sheets

U.S. PATENT DOCUMENTS

| | | | |
|---|---|---|---|
| 5,456,693 A | 10/1995 | Conston et al. | |
| 5,458,596 A | 10/1995 | Lax et al. | |
| 5,488,958 A | 2/1996 | Topel et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,588,960 A | 12/1996 | Edwards et al. | |
| 5,598,841 A | 2/1997 | Taniji et al. | |
| 5,614,204 A | 3/1997 | Cochrum | |
| 5,662,680 A | 9/1997 | Desai | |
| 5,672,153 A | 9/1997 | Lax et al. | |
| 5,674,243 A | 10/1997 | Hale | |
| 5,691,314 A | 11/1997 | Hodgen | |
| 5,697,942 A | 12/1997 | Palti | |
| 5,713,896 A | 2/1998 | Nardelia | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,759,154 A | 6/1998 | Hoyns | |
| 5,766,135 A | 6/1998 | Terwilliger | |
| 5,776,129 A | 7/1998 | Mersch | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,899,861 A | 5/1999 | Friemel et al. | |
| 5,910,484 A | 6/1999 | Haupert, Jr. | |
| 5,911,691 A | 6/1999 | Mochizuki et al. | |
| 5,921,933 A | 7/1999 | Sarkis et al. | |
| 5,922,008 A | 7/1999 | Gimpelson | |
| 5,941,889 A | 8/1999 | Cermak | |
| 5,979,453 A | 11/1999 | Savage et al. | 128/898 |
| 6,015,541 A | 1/2000 | Greff et al. | |
| 6,019,724 A | 2/2000 | Gronningsaeter et al. | |
| 6,032,673 A | 3/2000 | Savage et al. | 128/898 |
| 6,033,398 A | 3/2000 | Farley et al. | |
| 6,034,477 A | 3/2000 | Peeters et al. | |
| 6,035,238 A | 3/2000 | Ingle et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,106,473 A | 8/2000 | Violante et al. | |
| 6,152,874 A | 11/2000 | Looney et al. | |
| 6,231,515 B1 | 5/2001 | Moore et al. | |
| 6,254,601 B1 | 7/2001 | Burbank et al. | |
| 6,280,441 B1 | 8/2001 | Ryan | |
| 6,293,954 B1 | 9/2001 | Fogarty et al. | |
| 6,299,621 B1 | 10/2001 | Fogarty et al. | |
| 6,602,251 B2 * | 8/2003 | Burbank et al. | 606/45 |
| 2002/0183771 A1 | 12/2002 | Burbank et al. | |
| 2002/0188306 A1 | 12/2002 | Burbank et al. | |

FOREIGN PATENT DOCUMENTS

| | | |
|---|---|---|
| EP | 0 598 579 | 5/1994 |
| EP | 1 072 282 | 1/2001 |
| GB | 2 302 025 A | 1/1997 |
| GB | 2 302 025 | 1/1997 |
| GB | 2 311 468 A | 1/1997 |
| SU | 1 072 859 A | 2/1984 |
| WO | WO 95/02370 | 1/1995 |
| WO | WO 95/02371 | 1/1995 |
| WO | WO 96/05776 | 2/1996 |
| WO | WO 98/19713 | 5/1998 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/078521 | 10/2002 |

OTHER PUBLICATIONS

Brohim, Robert M. et al., "Development of Independent Vessel Security After Ligation With Absorbable Sutures or Clips", *The American Journal of Surgery*, Mar. 1993, vol. 165, pp. 345–348.

Burbank, Fred et al., "Uterine Artery Occlusion by Embolization or Surgery for the Treatment of Fibroids: A Unifying Hypothesis–Transient Uterine Ischemia", *The Journal of the American Association of Gynecologic Laparoscopists*, Nov. 2000, vol. 7, No. 7 Supplemental, pp. S3–S49.

Hay, D.L. et al., "Hemostasis in Blood Vessels After Ligation", *Am. J. Obstet. Gynecol.*, Mar. 1989, 160:3, pp. 737–739.

Hunerbein, M. et al., "Endoscopic Ultrasound–Guided Real Time Biopsy of Peri–Intestinal Tumors", *Surgical Technology International VII*, 1998, pp. 91–95.

O'Leary, James A., M.D., "Uterine Artery Ligation in the Control of Postcesarean Hemorrhage", *The Journal of Reproductive Medicine, Inc.*, 40(3):189–193 (Mar. 1995).

Schaefer, C.J. et al., "Absorbable Ligating Clips", *Surg. Gynecol. Obstet.*, 1982, 154:513–516.

"Mick 200 –TP Applicator Package", Mick Radio–Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostate Gland", Bruel & Kjaer Medical Systems, Inc., advertisement.

Bateman, William M.D., "Treatment of intractable menorrhagia by bilateral uterine vessel, Interruption", *Am. J. Obst. & Gynec.* 89(6):825–827 (Jul. 15, 1964).

Brigato, G. et al., "A Noninvasive Instrumental Method in Severe Postpartum Hemorrhages", *Minerva Ginecologica* 50(7–8):337–339 (1998).

Ravina, J. H. et al., "Arterial embolisation to treat uterine myomata", *The Lancet* 346:671–672 (Sep. 9, 1995).

Garza Leal, J. et al., "Myoma Treatment by Transient Uterine Ischemia" *The Journal of the American Assoication of Gynecologic Laparoscopists* 7(3):S31 (Aug. 2000).

Fuchs, Karl, "Afibrinogenemia Treated by Ligation of Uterine Arteries" *Gynacologic* 148:407–411 (1959).

O'Leary, James A, M.D. "Uterine Artery Ligation in the Control of Postcesarean Hemorrhage" *Am. J. Obst. & Gynec.* 94(7):920–924 (Apr. 1, 1996).

O'Leary, James L., M.D. et al., "Uterine artery ligation in the control of intractable postpartum hemorrhage" *Am. J. Obs. & Gynec.* 94(7):920–924 (Apr. 1, 1966).

International Search Report for PCT/US03/10551, mailed Jan. 2, 2004.

International Search Report for PCT/US04/03023 mailed Feb. 9, 2005.

International Search Report for PCT/US2004/038276, mailed Mar. 15, 2005.

International Search Report for PCT/US03/35815 mailed Jun. 30, 2004.

\* cited by examiner

DOPPLER DIRECTED SUTURING AND COMPRESSION DEVICE AND METHOD

BACKGROUND OF THE INVENTION

1. Field of the Invention

The present invention relates to devices, systems, and processes useful for locating and compressing a uterine artery of a female human patient, and more particularly to devices and systems capable of easily locating, compressing, ligating and/or monitoring or characterizing the blood flow through a uterine artery.

2. Brief Description of the Related Art

It has been proposed that occlusion of the uterine arteries of a human female patient can kill myomata, i.e., fibroids, because of the relative frailty of the fibroids to anoxia or hypoxia, and the relatively high resistance of uterine tissues to anoxia or hypoxia. See Burbank, Fred, M. D., et al, Uterine Artery Occlusion by Embolization or Surgery for the Treatment of Fibroids: A Unifying Hypothesis-Transient Uterine Ischemia, The Journal of the American Association of Gynecologic Laparoscopists, November 2000, Vol. 7, No. 4 Supplement, pp. S3–S49. U.S. Pat. No. 6,254,601, to Fred Burbank et al, entitled "Methods for Occlusion of the Uterine Arteries", describes numerous devices and methods useful for occluding a uterine artery by penetrating the tissue of the patient to access the uterine artery. The devices and methods described in Burbank '601 have been useful in occluding a uterine artery; there have been some difficulties involved with their use.

Specifically, the aligned orientations of the imaging device, e.g., Doppler ultrasound device, and the element which passes through the tissue of the patient to occlude the uterine artery can be, for some patients and for some procedures, difficult to maintain. Additionally, the devices and methods described in the '601 patent do not necessarily take advantage of the structure and symmetry of the female human anatomy to facilitate occlusion of a uterine artery. The devices and methods of the '601 patent also are not well adapted for performing blood flow studies of a uterine artery.

Current devices available for uterine artery identification and characterization include two-dimensional Doppler color flow ultrasound systems with vaginal, abdominal, or intra-cavity probes. Typical machines are manufactured and distributed by General Electric Medical Systems, Toshiba, and Acuson, among other sources.

These machines require an ultrasound technologist to utilize the vaginal probe and position the probe sensor array within the vagina, near the cervix, while looking at the ultrasound machine's display screen, position the probe, and then select an appropriate setting to evaluate blood flow. Currently available devices thus require a high degree of skill to identify and then position the Doppler gate approximately to obtain an optimum signal for characterizing the blood flow. During this time, the probe must be held in as steady a position as possible to eliminate erroneous readings and signals. As will be readily appreciated by those of skill in the art, prior devices are therefore difficult to use successfully.

Physicians, including gynecologists, have ligated the uterine artery surgically by using metal vascular clips or suture material, access having been achieved by surgical dissection. These surgical procedures have been performed by open abdominal surgery and laparoscopically, and require a great deal of surgical skill to access, identify, dissect, and ligate the uterine artery. This high skill requirement has limited the use of surgical ligation of the uterine arteries as a clinical alternative for treatment of uterine fibroids and other uterine disorders.

Ultrasound devices have been proposed for measuring blood flow in a blood vessel. See, e.g., U.S. Pat. Nos. 5,411,028, 5,453,575, 5,535,747, and 5,967,987

In an article published in 1964, Bateman reported that uterine artery vessel ligation or division, achieved via intra-abdominal surgery similar to hysterectomy, was effective in treating menorrhagia both with and without myomectomy. Bateman, W., M. D., "Treatment of intractable menorrhagia by bilateral uterine vessel interruption", 89 Am. J. Obstet. Gynecol. 825–827 (Harcourt Health Sciences, Jul. 15, 1964). While Bateman reported some success, this procedure involves opening the abdominal cavity, with the known attendant risks and disadvantages.

Ligation devices have previously been proposed. These prior ligation devices have typically been used in laparoscopic procedures, and have typically required that the anatomical feature of interest be dissected or visualized prior to ligation of that feature. Other ligation devices require the penetration of a tissue bundle encapsulating the anatomical vessel in order to perform location and ligation of the vessel.

Ligation has also been effected by surgically utilizing metal vascular clips. The disadvantage in this technique is that the procedure must be performed laparoscopically and requires a great deal of surgical skill to access, identify, dissect, and ligate the uterine arteries, and is permanent. Because of the high skilled involved, the process has limited the use of surgical ligation of the uterine arteries as a clinical alternative to uterine fibroid treatment.

There therefore remains a need in the art to develop apparatus and methods which further assist a medical practitioner in accessing, occluding, and/or measuring the blood flow characteristics in a uterine artery.

SUMMARY OF THE INVENTION

According to a first aspect of the invention, a device useful for compressing a uterine artery of a female human patient comprises a first jaw having a distal end and a first distal end face, a second jaw having a distal end and a second distal end face, a pivot, the first jaw and the second jaw movably attached at the pivot, wherein the first and second jaws are configured and arranged so that when the first and second jaws are pivoted relative to each other at the pivot in a first direction to a relatively closed orientation, the first and second distal end faces are oriented toward each other; and at least one Doppler crystal mounted in one of the first and second distal end faces, the at least one Doppler crystal having a direction of view, the direction of view being toward the other of the first and second distal end face in the relatively closed orientation.

According to yet another aspect of the present invention, a method of occluding a uterine artery of a female human patient, the patient having a uterus, a cervix with a cervical os, and a vaginal wall with a vaginal fornix, comprises pushing a compressing member toward the uterine artery until the compressing member reaches the vaginal fornix, pushing the compressing member upwardly to distend the vaginal wall at the vaginal fornix adjacent to and on two substantially opposite sides of the uterine artery, and compressing the uterine artery with the compressing member.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DESCRIPTION OF THE PREFERRED EMBODIMENTS

Referring to the drawing figures, like reference numerals designate identical or corresponding elements throughout the several figures.

Figure 1:
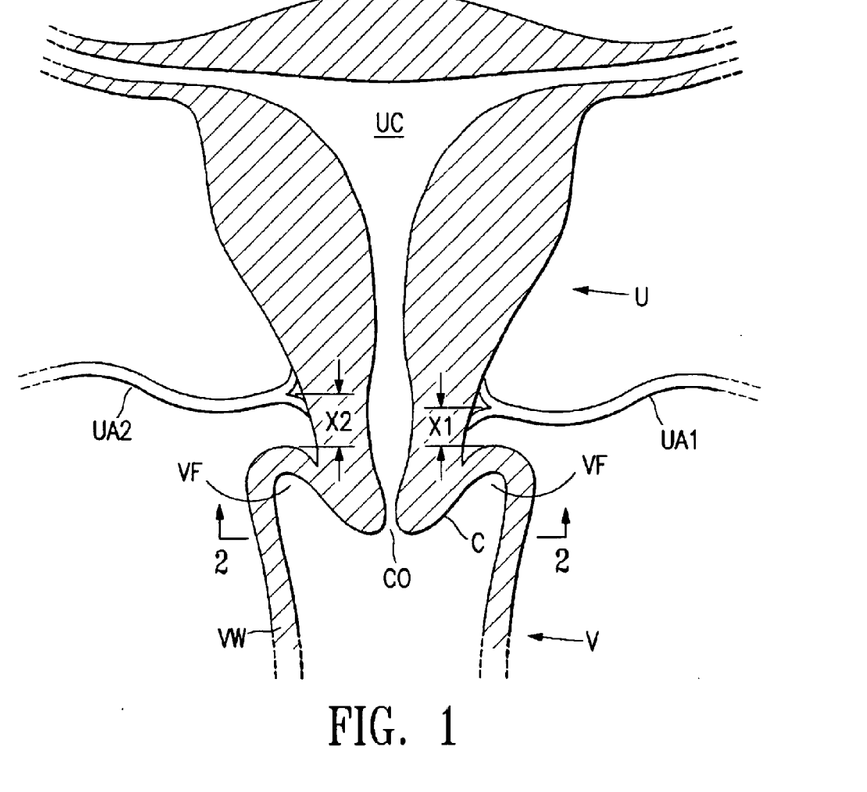
FIG. 1 illustrates simplified cross-sectional view of a uterus, cervix, and vagina of a female human in a coronal plane.

The inventors herein have discovered that the uterine arteries of female humans typically are about 3 cm or less from the vaginal wall at the vaginal fornix where the uterine artery meets the uterus, although the uterine arteries for a single patient sometimes are spaced at slightly different distances (see distances X1 and X2 in FIG. 1). The inventors herein have also discovered that the right uterine artery is typically positioned between about the 1 and 5 o'clock (see FIG. 2) positions, and more frequently between about 2 and 4 o'clock; and that there is typically symmetry between the uterine arteries, i.e., that the left uterine artery is typically positioned between about the 7 and 11 o'clock positions, and more frequently between about 8 and 10 o'clock. The inventors herein have also discovered that the cervix can be used as a platform and a landmark from which to locate and access a uterine artery because of the axial symmetry of the cervix and it's generally cylindrical or frustoconical exterior shape. See also U.S. application Ser. No. 09/908,815, filed Jul. 20, 2001, to Fred Burbank et al. ("'815 application"), co-assigned with the present application, for additional discussions of the anatomy of the uterus, cervix, and vaginal wall, the entire contents of which are incorporated by reference herein.

Figure 2:
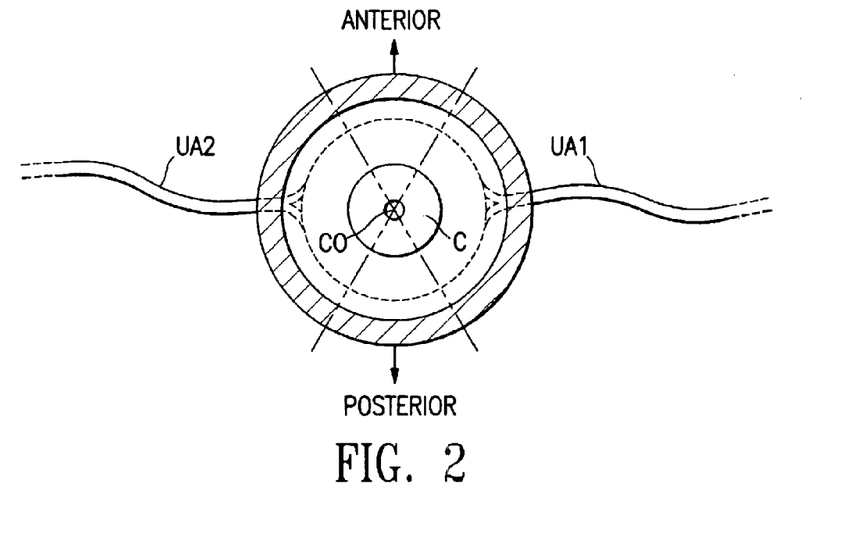
FIG. 2 illustrates a plan view taken at line 2—2 in FIG. 1 along an axial or transverse plane.

FIGS. 1 and 2 illustrate two different views of the uterus, cervix, vagina, and uterine arteries of a female human patient. Because reference will be made throughout this description to some of these anatomical structures, a brief discussion of this portion of the female human anatomy may prove useful. A uterus U includes a uterine cavity UC. The vagina V has a vaginal wall VW which extends upward to the vaginal fornix VF. The cervix C is (typically) centrally located and extends from the uterus U to a point typically somewhat below the vaginal fornix VF, and includes a cervical os CO which leads to the uterine cavity UC. Uterine arteries UA1 and UA2 lead to the uterus U from the inferior iliac artery (not illustrated). In this following descriptions, the orientations of the uterine arteries UA1 and UA2 will be described in terms of a clock face, i.e., the positions of the uterine arteries will be identified as corresponding to particular times on a clock. In this context, 12 o'clock is the anterior direction from the center of the cervical os CO, 6 o'clock is posterior therefrom, 3 o'clock is laterally to the right (the patient's left side, see FIG. 2), and 9 o'clock is laterally to the left (the patient's right side, see FIG. 2). As will be readily apparent to those of skill in the art, the use of the clock face as a reference frame is used merely to simplify the discussions herein, and other reference frames, such as degrees or radians from a known or ascertainable reference line, can be interchangeably used herein.

The devices in accordance with the present invention are sized to be insertable through the vagina of a female human patient, along a side of the exterior of the cervix, and to the vaginal wall at the vaginal fornix.

Manipulation of a compressor according to the present invention compresses the uterine artery, at least partially, and optionally completely, stopping the blood flow through the artery. As described in the '815 application, cessation of blood flow through the uterine artery can have beneficial effects for the patient, including the treatment of fibroids by limiting the blood supplied to the fibroids in the uterus.

Figure 3:
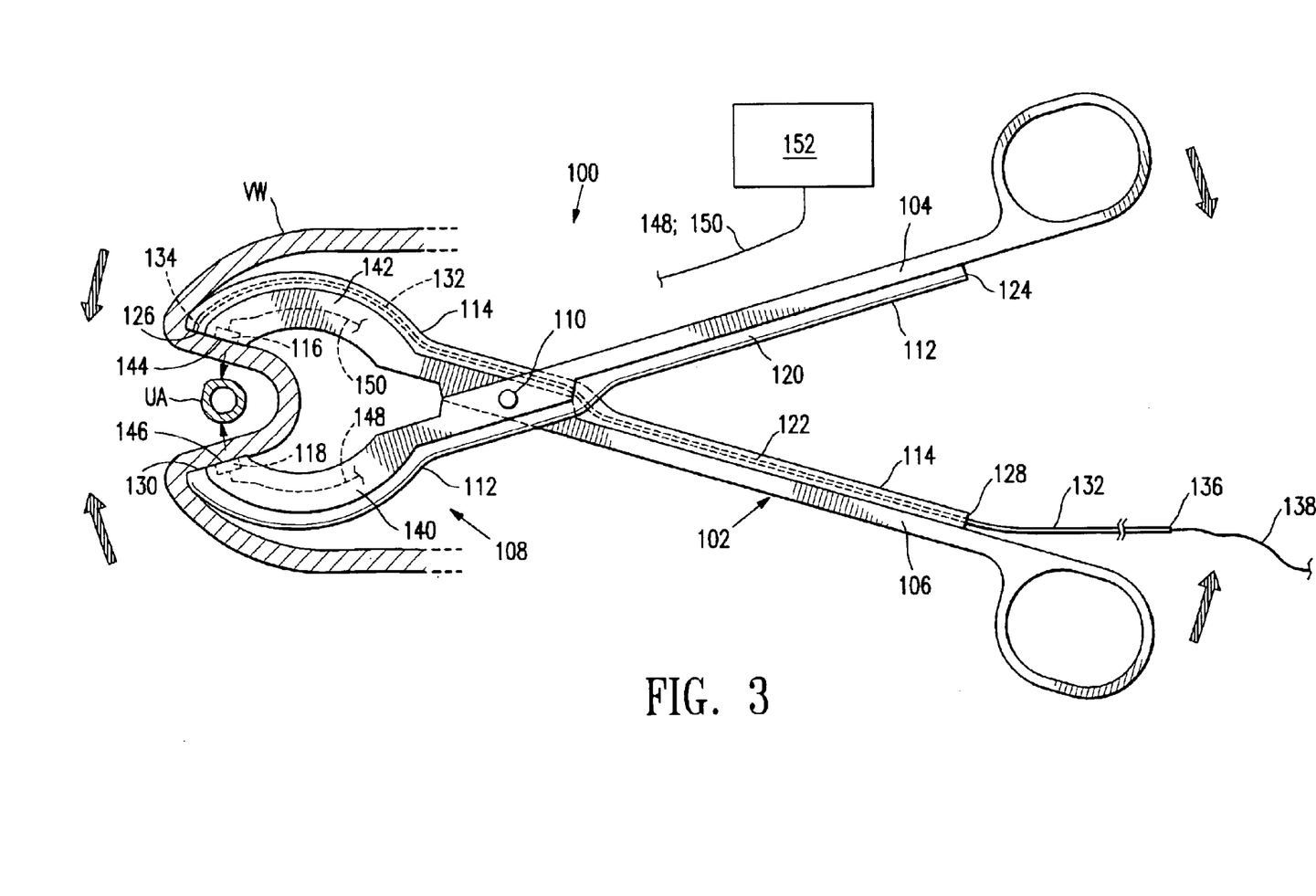
FIG. 3 illustrates a side (right sagital) elevational view of an exemplary device in accordance with the present invention in position adjacent to the cervix of the patient and invaginating the vaginal wall of the patient.

FIG. 3 illustrates an exemplary compression and ligation device 100 in accordance with the present invention. An aspect of the present invention includes that the device 100 can optionally, and preferably, include one or more Doppler crystals or chips to permit location of a uterine artery or arteries or other blood vessels, and monitoring the blood flow through the vessel(s).

Turning now to FIG. 3, the device 100 includes a handle 102 including first and second arms 104, 106, and a distal clamping and/or ligation portion 108. The two arms 104, 106 are joined together at a hinge or pivot 110 about which the two arms can move. Attached to or formed in at least the distal portion 108 is a pair of hollow, tube-like guide channels 112, 114 which provide a guided pathway for a suture leader 132 with an attached length of suture or ligation material 138 to be passed around a blood vessel of interest, as described in greater detail below. Preferably, the guide channels 112, 114 extend proximally so that they are more easily accessible from the proximal end of the device 100.

The device 100 is illustrated in FIG. 3 in a position to one side of the cervix C (see FIGS. 1, 2) after having been advanced upwardly to invaginate the vaginal wall VW at the vaginal fornix VF. The uterine artery UA on that side of the uterus is illustrated in a position somewhat between the open jaws of the device 100, and prior to being either compressed or ligated.

The distal portion 108 of the device 100, according to preferred embodiments of the present invention, includes at least one, and optionally a plurality, of Doppler chips or crystals 116 mounted in or otherwise attached to the distal ends of the distal portion. As suggested by the arrow illustrated in FIG. 3, the direction of view of the Doppler chip 116 is laterally across the device itself outward from the end face 144 and toward the end face 146. Further optionally, the device 100 can include a plurality of Doppler chips, mounted at one distal end face 144, a chip 116, 118 in each of the end faces 144, 146, a plurality of chips mounted in one end face, a plurality of chips mounted in both end faces, and/or combinations thereof.

The directions of view of the chip or chips incorporated into the device 100 are selected so that, as illustrated in FIG. 3, when the vaginal wall is invaginated by the open jaws of the device 100, the Doppler chip(s) can send Doppler signals at and receive Doppler signals from the uterine artery UA.

With the direction(s) of view of the Doppler chip(s) selected in this manner, the Doppler chip(s) can be used to determine the location of the uterine artery UA relative to the end faces 144, 146 of the device 100. More specifically, the Doppler data generated by the Doppler chip(s) can be used to determine when the vaginal wall has been invaginated sufficiently that the uterine artery UA is between the end faces of the device 100. Furthermore, the Doppler data can be reviewed to establish what is a base blood flow through the artery for future reference. This knowledge of the placement of and blood flow through the uterine artery can be useful to the practitioner for deciding, among other things, whether to compress and/or ligate the artery, or merely to establish a baseline blood flow through the artery for future reference.

Turning back to FIG. 3, each of the guide channels 112, 114 includes a lumen 120, 122, which extends between open distal and proximal openings or ports, 126, 128, 124, 130. A suture leader 132 is sized to be able to be advanced within either or both lumina 120, 122, and has a distal end 134 and a proximal end 136 to which is attached a length of suture or ligation material 138. The suture leader is sized and formed of a material so that it can be pushed up through one of the guide channels 112, out the distal opening 126, penetrate the vaginal wall, pass through the tissues behind the vaginal wall and behind the uterine artery UA, again through the vaginal wall, into the distal port 130 of the guide channel 112, and through the other guide channel 114 (see FIG. 4). As the material 138 is attached to the proximal end 136 of the leader 132, the material is pulled along this same path. It is therefore also an aspect of the present invention that the length of the suture leader is selected so that it can loop through the two guide channels, as described above, and the distal end 134 can be retrieved from the proximal opening 124, with the proximal end 136 of the leader still exposed proximally of the opening 128. By way of example and not of limitation, one suitable leader 132 is formed of 0.0020 inch (outer diameter) stainless steel wire and is about 20 inches long. Other suitable materials include nitinol (NiTi), and the leader's cross-sectional shape can be any of those well known to those of skill in the art, including rectangular, square, and round. Further optionally, the cross-sectional shapes of the suture leader 132 and the lumina 120, 122 of the guide channels 112, 114 can be selected together to ease passage of the suture leader through the lumen, while minimizing the dead space between the suture leader and the guide channel. Additionally, the material of the ligation material 138 can be either resorbable, for which removal of the material from the patient is not necessary, or non-resorbable, for which eventual removal of the material from the patient is indicated for most patients.

The jaws 140, 142 of the device 100 are preferably generally C-shaped in at least a portion of their length. The curve of the C-shape creates an area or volume between the two jaws 140, 142, in which the tissue of the vaginal wall VW, etc., can reside when the jaws are clamped down onto a uterine artery, with less or no compression. The reduction in or lack of compression of these more proximal tissues can assist in maintaining the position of the uterine artery UA relative to the end faces 144, 146. As will be readily appreciated by those of skill in the art, if the tissues proximal of the uterine artery UA are under pressure, this can tend to push the tissues and the uterine artery upwardly (distally) away from the device 100, and out of the space immediately between the end faces 144, 146. Therefore, the optional provision in the device 100 of an area or volume between the jaws 140, 142 in which entrapped tissues are exposed to less pressure from the jaws (see FIG. 4) is another aspect of the present invention. According to one embodiment of the present invention, the distance between the pivot 110 and the distal openings 126, 130, is at least about 2 inches, and preferably about 3 inches, to provide this volume to accommodate proximal tissues. As will be readily appreciated by those of skill in the art, smaller or larger dimensions can be alternatively selected, and optionally only one of the jaws can be formed with a C-shape or similar shape.

The Doppler chip(s) 116, 118 are in signal communication with a Doppler signal processing and/or display device 152 via leads 148, 150. As such devices 152 are well understood by those of skill in the art, so further description will be given herein.

As discussed above, the devices of the present invention preferably include at least one, and optionally a plurality of Doppler ultrasound crystals oriented with the viewing direction of the crystals pointed laterally, as suggested by the arrows in FIG. 3. While a plurality of crystals can be advantageous in providing more data about the flow of blood through the uterine artery of interest, the additional data requires additional manipulation that can increase the complexity and cost of the device. Thus, it may in some circumstances be advantageous to provide fewer, or only a single, crystal to reduce the complexity of the Doppler data that must be interpreted.

The Doppler crystals 116, 118 are preferably positioned at the distal end faces 144, 146 of the device so that any data derived from the signals received by the Doppler crystals can be more easily correlated to the distance of the uterine artery from the distal end, and can verify that the uterine artery is between the two end faces. By way of example and not of limitation, the Doppler chip(s) can be positioned about 1 cm proximally of the channel opening on the same jaw 140, 142 as the Doppler crystal. The Doppler crystals can be integrated into the devices of the present invention, e.g., molded into the device itself, or alternatively can be removably mounted in the device. By way of example and not of limitation, the Doppler crystals 116, 118 can each be in a Doppler probe which is received in a correspondingly configured holder (see, e.g., a hole or cutouts in one of both of the jaws 140, 142) formed in distal portions of the device. While many commercially available Doppler probes are suitable in the present invention, a Vascular Technology, Inc., (Lowell, Mass.) 8 MHz Doppler probe, or a Koven 8 MHz Doppler probe (Koven, St. Louis, Mo.), can be used as a Doppler probe 214i, 216i.

Those of skill in the art will recognize that the frequency of the Doppler crystal will change the viewing angle of the crystal. One aspect of the present invention is the use of Doppler crystals which permit Doppler data to be gathered at distances up to about 3 cm, so that when the compressor on which the Doppler crystals are mounted is pushed against the vaginal wall at the vaginal fornix VF, the Doppler crystals will received signals back from the uterine artery of interest. Thus, while many different Doppler crystals are suitable in the present invention, those which operate at about 8 MHz have been found to be particularly suitable.

The signals from the Doppler crystals or probes are transmitted to a suitable signal processor 152 (see FIG. 3), which displays data derived from the signals. According to yet further aspects of the present invention, the data from each of the Doppler crystals is either manually or automatically examined to ascertain if the waveform received by the crystal is representative of the blood flow through a uterine artery UA1. Because the Doppler crystals are selected to have relatively narrow angles of view, the process of examining the signals received by each crystal will reveal which crystal is pointed most directly at the uterine artery.

Again with reference to the drawing figures, other aspects of the present invention include methods of finding, evaluating the blood flow through, compressing, and/or ligating a uterine artery. A device in accordance with the present invention, such as device 100, is positioned inside the vagina of the patient, with the jaws 140, 142 positioned to one side of the cervix C in the vaginal fornix VF. The jaws 140, 142 are opened, and the device 100 further advanced upwardly (toward the uterine artery behind the vaginal wall). The distal ends of each of the jaws, generally in the area of the openings 126, 130, and of the end faces 144, 146, push and invaginate the vaginal wall on opposite sides of the uterine artery. The presence of the uterine artery generally between the end faces 144, 146 can be confirmed by the Doppler data sent and received by the chip(s) 116, 118; if the uterine artery is present, a Doppler signal indicative of an artery will be observed, while absence of the uterine artery will be detected by the lack of such blood flow data.

In the event the uterine artery is not between the end faces 144, 146, the device 100 can be repositioned and/or the vaginal wall again invaginated. When the Doppler data indicates that the uterine artery UA is between the end faces 144, 146, the practitioner has several options. First, however, the practitioner can verify that the uterine artery UA is directly between the end faces 144, 146, by moving the device 100 slightly distally and slightly proximally. For example, if the Doppler data indicates a stronger Doppler signal when the device 100 is moved distally (upwardly), then the uterine artery is located more distal than the previous location of the device; similarly, if distal movement of the device produces a weaker Doppler signal, then the uterine artery is located more proximal. By using this methodology, the practitioner can easily and quickly determine that the uterine artery is located substantially between the end faces 144, 146, and is located proximally of the guide channel distal openings 126, 130.

Figure 4:
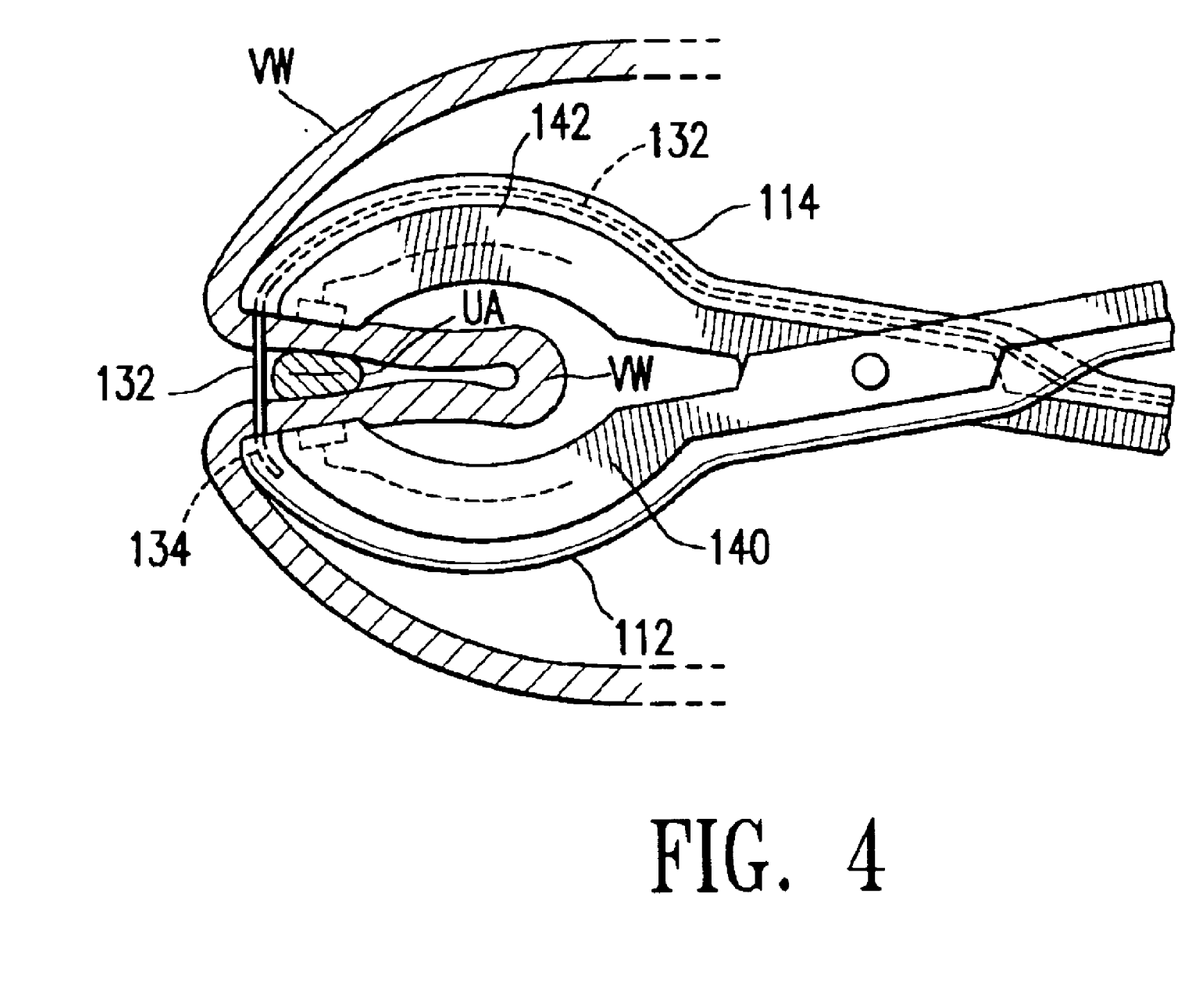
FIG. 4 illustrates a view similar to that illustrated in FIG. 3, with a compressed uterine artery.

With the device 100, and more particularly the jaws 140, 142, positioned with the uterine artery UA between the end faces 144, 146, the practitioner can choose between compressing the uterine artery by closing the jaws of the device, pushing the suture leader 132 behind the uterine artery to pass the material 138 around the uterine artery, or both (see FIG. 4). While the exact sequence is not critical, a preferred embodiment of the present invention includes: the uterine artery is first compressed by manipulating the handles 104, 106 to compress the uterine artery between the end faces 144,146; the suture leader 132 is passed through the vaginal wall, behind the uterine artery, and again out through the vaginal wall, pulling the material 138 behind the uterine artery and out the proximal opening 124; the suture material is separated from the leader and formed into a ligature to ligate the uterine artery in a closed, compressed condition; and the jaws are opened and the device removed, leaving the ligature in place closing the uterine artery. During any part of a method of the present invention, the Doppler data from the Doppler chip(s) can be used to determine if blood flow has stopped in the uterine artery.

Once it has been established that the blood flow through the uterine artery or arteries has stopped for a therapeutically effective period of time, the practitioner can release the jaws, remove the ligature, or both from the patient. In the context of device 100, the practitioner opens the jaws, and retracts the device 100 from along the one side of the cervix of the patient. As used herein, the term therapeutically effective time and its equivalents are used as in U.S. patent application Ser. No. 09/556,934, filed Apr. 21, 2000, by Burbank et al., and U.S. patent application Ser. No. 09/908,815, filed Jul. 20, 2001, by Burbank et al., the entireties of both of which are incorporated herein by reference. As most patients have two uterine arteries in which a practitioner may want to effect hemostasis, the method(s) described above can optionally be performed on the other uterine artery, either at substantially the same time, or after the first uterine artery has been compressed.

According to a preferred aspect of the present invention, the ligature is used as the mechanism by which the uterine artery or arteries are compressed for most or all of the therapeutically effective time, because the volume of tissue compressed by the relatively thin material 138 is much less than that compressed by the jaws 140, 142. With less tissue experiencing the compressive pressure and force of the material 138, there can be less concern over pressure-induced tissue necrosis.

The end faces 144, 146 may optionally be formed in or as a part of an integral or removable pad (not illustrated) at the distal ends of the jaws 140, 142. Further optionally, the pad(s) can configured or formed of a material which provides additional friction or grip between the vaginal wall VW and the device 100. The variations of the textures may include plastic ridges, foam, a textile type padding, metal or plastic teeth or fangs that protrude from the clamp face, or combinations thereof, to provide for more grip or bite into the tissue.

The present invention also relates to devices, systems, and processes which can be useful in treating dysfunctional uterine bleeding (DUB). As the skilled artisan readily appreciates, DUB can be a very frustrating and troublesome condition because the actual cause of the bleeding is, by definition, unknown. Stated somewhat differently, DUB is a diagnosis of exclusion; if a woman has menorrhagia and no organic abnormality can be identified, she is given the diagnosis of DUB. Women with DUB are debilitated just as are women with fibroids and menorrhagia: they can be socially restricted during times of high menstrual blood loss and are anemic. Other aspects of the present invention relate to treating a patient who is diagnosed with DUB by compressing one or both uterine arteries, either serially or simultaneously, so that the uterine blood supply is greatly diminished or completely cut off. Without the blood supplied by the uterine arteries, the uterus stops bleeding, which can permit the medical practitioner to better diagnose the patient's condition. Without being limited to a particular theory, it is also posited herein that at least some cases of DUB can be treated effectively by uterine artery compression and/or ligation as described herein, that is, that DUB will not reoccur upon reestablishment of the blood supply to the uterus through the uterine arteries. To put it somewhat colloquially, the apparatus and methods of the present invention can be used to 'reset' the uterus by going through a period of induced anoxia or hypoxia. The Bateman article, mentioned briefly above, lends support to this hypothesis.

The present invention also includes as an aspect the treatment of bleeding associated with Caesarian section. Caesarian delivery results in at least two sources of post partum bleeding: blood loss at the Caesarian incision site; and blood loss at the placental separation site. Generally, natural mechanisms control blood loss at the placental separation site, while blood loss at the Caesarian incision site is typically achieved by suturing the two margins of the incision firmly together. The pressure of the sutures slows blood flow at the incision site and clot then forms; however, until sufficient suturing has been accomplished, blood loss occurs. Because suturing the Caesarian incision site is performed under urgent circumstances, to minimize blood loss, suturing quality of the incision is performed as if the uterus were composed of one layer of tissue, instead of three. Consequently, the outcome of this prior method is suboptimal at the endometrial, myometrial, and serosal levels. Thus another aspect of the present invention is the use of devices and/or the performance of methods in accordance with the present invention instead of, or in conjunction with, these prior suturing methods to treat Caesarian delivery bleeding. More specifically, devices and/or methods of the present invention are used and/or implemented to slow or stop blood flow to the uterus through the uterine arteries immediately after a baby is delivered. Subsequently, Caesarian incision repair can be performed in a manner that optimizes surgical closure, without worry about blood loss control at the time of closure.

The present invention also includes as an aspect the treatment of bleeding associated with Post Partum Hemorrhage (PPH). PPH is defined in the medical literature as the estimated loss of more than 500 ml of blood following delivery of a baby. It can occur for a wide variety of reasons and occurs following at least 5% of deliveries. Most often it occurs because the uterus fails to contract following placental separation (uterine atony). Without adequate post partum uterine contractions, blood does not slow enough in the uretoplacental arteries to clot. Without clot formation in the uretoplacental arteries, bleeding from the uretoplacental arteries persists.

Many treatments exist for hemorrhage secondary to uterine atony, including massage of the uterus through the abdominal wall, administration of drugs that encourage myometrial contraction (e.g., oxytocin, methylergonovine, and prostaglandins), uterine cavity packing with, e.g., cloth materials, balloon tamponade of the uterine cavity, bilateral surgical ligation of the uterine artery, ovarian arteries, or internal iliac artery, bilateral uterine artery embolization, suturing through the uterus (e.g., B-Lynch Brace technique), and hysterectomy. Many of the existing treatments are ineffective; others are overly complex, invasive, and slow to initiate.

According to aspects of the present invention, when it is recognized that bleeding has not stopped normally as it should after delivery, devices and/or methods in accordance with the present invention can be employed as described herein to slow or stop PPH.

The present invention extends at least to include devices and methods including combinations of all of the features and steps described above. By way of example and not of limitation, the Doppler chip(s) described herein can be incorporated into any of the exemplary devices described herein, arranged at the distal end(s) of the device(s) as will be readily apparent to one of skill in the art. In a similar manner, methods of the present invention can include, but are not limited to, any one or combinations of the steps described above. Furthermore, any of the above described devices and methods which are described as useful for occluding a single uterine artery can be incorporated into bilateral devices and methods, that is, two of the unilateral devices can be joined into a single, bilateral device, with each of the two unilateral devices positioned in the bilateral device to access and/or locate a single uterine artery, and the steps of a method for accessing and/or locating a single uterine artery can be performed bilaterally, either serially or simultaneously.

Devices in accordance with the present invention can be formed of any of numerous materials, as will be readily apparent to those of skill in the art. By way of example and not of limitation, the devices can be formed of: surgical stainless steel, nitinol (NiTi), titanium, or other biocompatible and preferably sterilizable metals; any of a number of thermoplastic and thermoset materials which are sufficiently biocompatible and sterilizable; and combinations thereof.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. An intravaginal occlusive device for occluding a uterine artery of a female human patient comprising:
   a. a first elongated member having a first jaw with a distal end, a first ligature guide formed on the first jaw, a pivoted proximal end and an inner surface between the proximal and distal end which forms a tissue receiving recess and having a handle extending proximal to the pivoted proximal end;
   b. a second elongated member having a second jaw with a distal end, a second ligature guide formed on the second jaw, a pivoted proximal end and an inner surface between the proximal and distal end and having a handle extending proximal to the pivoted proximal end; and
   c. at least one Doppler crystal attached to the distal end of at least one of the first or second jaws having a direction of view toward the distal end of the other jaw when in a closed configuration to detect a uterine artery disposed between the distal ends of the first and second jaws.

2. A device in accordance with claim 1, wherein the at least one Doppler crystal is releasably attached to the one of the first and second distal end faces.

3. A device in accordance with claim 1, wherein the at least one Doppler crystal is integrally formed in the one of the first and second distal end faces.

4. A device in accordance with claim 1, wherein the at least one Doppler crystal comprises at least one Doppler crystal attached to each of the first and second distal end faces.

5. A device in accordance with claim 1, wherein the at least one Doppler crystal comprises a plurality of Doppler crystals attached to each of the first and second distal end faces.

6. A device in accordance with claim 1, wherein the at least one Doppler crystal comprises a plurality of Doppler crystals attached to the one of the first and second distal end faces.

7. A device in accordance with claim 1, wherein
   the first ligature guide has a proximal opening, a distal opening, and a lumen extending between the proximal and distal openings; and
   the second liguature guide has a proximal opening, a distal opening, and a lumen extending between the proximal and distal openings.

8. A device in accordance with claim 7, wherein the first ligature guide distal opening and the second ligature guide distal opening are oriented toward each other when the jaws are in a closed configuration.

9. A device in accordance with claim 7, further comprising:
   a suture leader sized and configured to pass through the first ligature guide lumen and the second ligature guide lumen; and a length of ligation material attached to the suture leader.

10. A device in accordance with claim 1, wherein said inner surfaces of both the first and second jaws define tissue receiving recesses.

11. A device in accordance with claim 1, wherein at least one of the first and second jaws is C-shaped.

12. A device in accordance with claim 10, wherein both of the first and second jaws are C-shaped.

13. A method of occluding a uterine artery of a female human patient, the patient having a uterus, a cervix with a cervical os, and a vaginal wall with a vaginal fornix, comprising:
   a. providing a compressing member comprising,
      i. a first elongated member having a first jaw with a distal end, a first ligature guide on the first jaw, a pivoted proximal end and an inner surfaces between the proximal and distal end which forms a tissue receiving recess and having a handle extending proximal to the pivoted proximal end;
      ii. a second elongated member having a second jaw with a distal end, a second ligature guide on the second law, a pivoted proximal end and an inner surface between the proximal and distal end and having a handle extending proximal to the pivoted proximal end; and
      iii. at least one Doppler crystal attached to the distal end of at least one of the first or second laws having a direction of view toward the distal end of the other jaw when in a closed configuration to delect a uterine artery disposed between the distal ends of the first and second jaws;
   b. advancing the compressing member within a patient's vagina toward a region of the patient's vaginal fornix adjacent to a uterine artery until the compressing member reaches the vaginal fornix;
   c. manipulating the compressing member effective to distend the vaginal wall at the vaginal fornix adjacent to and on two substantially opposite sides of the uterine artery by the first and second laws;
   d. pressing a portion of the vaginal fornix wall with the first and second jaws of the compressing member and closing the jaws to detect the underlying uterine artery; and
   e. passing ligature through one of the ligature guides, through the tissue between the closed jaw distal to the uterine artery and through the other ligature guide, and tightening the ligature about the uterine artery so as to occiude the uterine artery.

14. A method in accordance with claim 13, further comprising sensing blood flow through the uterine artery with at least one Doppler crystal having a direction of view.

15. A method in accordance with claim 14, wherein said direction of view comprises a direction along a line passing through two substantially opposite sides of the uterine artery, and wherein the step of sensing blood flow through the uterine artery comprises sensing blood flow along said direction of view.

16. A method in accordance with claim 14, wherein the ligature at least partially occludes the uterine artery for a therapeutically effective time after the at least one Doppler crystal indicates that blood flow through the uterine artery has stopped.

17. A method in accordance with claim 13, wherein the uterine artery is at least partially occluded by compressing the uterine artery between two end faces of the two pivoting jaws.

* * * * *

UNITED STATES PATENT AND TRADEMARK OFFICE
CERTIFICATE OF CORRECTION

| | | |
|---|---|---|
| PATENT NO. | : 7,207,996 B2 | Page 1 of 1 |
| APPLICATION NO. | : 10/115422 | |
| DATED | : April 24, 2007 | |
| INVENTOR(S) | : Burbank et al. | |

It is certified that error appears in the above-identified patent and that said Letters Patent is hereby corrected as shown below:

Column 11, line 16:
Change "inner surfaces" to -- inner surface --.

Column 12, line 10:
Change "closed jaw" to -- closed jaws --.

Signed and Sealed this

Third Day of July, 2007

JON W. DUDAS
*Director of the United States Patent and Trademark Office*